(12) United States Patent
Scott

(10) Patent No.: US 11,033,522 B2
(45) Date of Patent: Jun. 15, 2021

(54) FREE AMINO ACID PREPARATION AND USES THEREOF

(71) Applicant: David C Scott, Aliso Viejo, CA (US)

(72) Inventor: David C Scott, Aliso Viejo, CA (US)

( * ) Notice: Subject to any disclaimer, the term of this patent is extended or adjusted under 35 U.S.C. 154(b) by 231 days.

(21) Appl. No.: 15/673,214

(22) Filed: Aug. 9, 2017

(65) Prior Publication Data

US 2018/0042879 A1 Feb. 15, 2018

Related U.S. Application Data

(60) Provisional application No. 62/372,438, filed on Aug. 9, 2016.

(51) Int. Cl.
| | | |
|---|---|---|
| *A61K 31/198* | (2006.01) | |
| *A61K 45/06* | (2006.01) | |
| *A61K 9/08* | (2006.01) | |
| *A61K 9/14* | (2006.01) | |
| *A23L 33/175* | (2016.01) | |
| *A61K 31/4172* | (2006.01) | |
| *A61K 9/48* | (2006.01) | |
| *A61K 31/405* | (2006.01) | |

(52) U.S. Cl.
CPC .......... *A61K 31/198* (2013.01); *A23L 33/175* (2016.08); *A61K 9/08* (2013.01); *A61K 9/14* (2013.01); *A61K 9/4833* (2013.01); *A61K 31/405* (2013.01); *A61K 31/4172* (2013.01); *A61K 45/06* (2013.01); *A61K 2300/00* (2013.01)

(58) Field of Classification Search
CPC .......... A61K 31/198; A61K 9/08; A61K 9/14; A61K 9/4833; A61K 31/405; A61K 31/4172; A61K 45/06; A61K 2300/00; A23L 33/175
USPC .......................................... 514/561
See application file for complete search history.

(56) References Cited

U.S. PATENT DOCUMENTS

| | | |
|---|---|---|
| 2008/0213246 A1 | 9/2008 | Ziff |
| 2008/0317886 A1 | 12/2008 | Sparkman |
| 2011/0081329 A1 | 4/2011 | Smith et al. |
| 2013/0018102 A1 | 1/2013 | Dente, III et al. |
| 2015/0011500 A1* | 1/2015 | Dake ............... A61K 35/57 514/54 |

FOREIGN PATENT DOCUMENTS

| | | |
|---|---|---|
| WO | 2007056179 | 5/2007 |
| WO | 2008112561 | 9/2008 |
| WO | 2015006287 | 1/2015 |

* cited by examiner

*Primary Examiner* — Yevgeny Valenrod
(74) *Attorney, Agent, or Firm* — Fish IP Law, LLP

(57) ABSTRACT

Compositions containing free amino acids have been found to provide effective pain relief in less than five minutes following administration. Suitable compositions include free leucine, free isoleucine, and free valine in a leucine:isoleucine:valine weight ratio of about 1.9:1:1.3. Palatability is improved by the addition of free glycine, such that sweeteners or other flavorants are not necessary. The composition can be a two part formulation in which certain amino acids are provided as a capsule or tablet in order to improve palatability.

12 Claims, No Drawings

FREE AMINO ACID PREPARATION AND USES THEREOF

This application claims priority to U.S. Provisional Application No. 62/372,438, filed on Aug. 9, 2016. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is amino acid preparations and uses thereof, more particularly amino acid preparations that are effective in treating pain.

BACKGROUND

The following description includes information that may be useful in understanding the present invention. It is not an admission that any of the information provided herein is prior art or relevant to the presently claimed invention, or that any publication specifically or implicitly referenced is prior art.

The background description includes information that may be useful in understanding the present invention. It is not an admission that any of the information provided herein is prior art or relevant to the presently claimed invention, or that any publication specifically or implicitly referenced is prior art.

Amino acids are the fundamental units of the polypeptides and proteins of the human body. Humans can synthesize some amino acids through normal metabolic processes. Other amino acids, designated as essential amino acids, cannot be synthesized by humans and must be obtained by consumption. Essential amino acids include phenylalanine, valine, threonine, tryptophan, methionine, leucine, isoleucine, and lysine. Other amino acids are considered to be conditionally essential, and the ability of humans to synthesize these can be impacted by certain conditions and/or disease states (e.g. prematurity, metabolic stress). Conditionally essential amino acids include arginine, cysteine, glycine, glutamine, proline, and tyrosine. Lack of essential amino acids (and, under certain circumstances, conditionally essential amino acids) can result in malnutrition disease.

The USDA has developed guidelines for minimal consumption of essential amino acids, which are generally obtained by consuming protein-containing foods. Proteins are broken down through enzymatic processes in the gut and gradually absorbed into the body. Free amino acids (i.e. amino acids that are not part of a polymer, peptide, polypeptide, or protein) can also be consumed directly.

Various attempts have been made to provide preparations that include free amino acids and that can generate a beneficial effect on the human body. For example, United States Patent Publication No. 2008/0213246 (to Ziff and Ziff) describes a mixture of vitamins, herbs, enzymes, and an amino acid that can reduce pain from various sources after about two hours from administration. All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. Similarly, United States Patent Application No. 2008/0317886 (to Sparkman) describes a complex composition that includes various sugars, essential amino acids, protein, anti-inflammatory agents, performance enhancing agents, anti-oxidants, and analgesics that can prevent inflammation and muscle soreness. Neither of these, however, are described as providing rapid and effective relief of existing pain.

Thus, there is still a need for a free amino acid containing composition that provides rapid and effective relief of pain and other conditions of the human body.

SUMMARY OF THE INVENTION

The inventive subject matter provides compositions and methods for the rapid (e.g. less than five minutes) and effective treatment of pain using a composition that includes free amino acids, particularly a free amino acid composition that includes phenylalanine and tyrosine in a 3.4 to 1 weight ratio.

One embodiment of the inventive concept is an amino acid preparation for human consumption, that includes free amino acid forms of phenylalanine, tyrosine, and alanine, along with at least one free amino acid selected from glutamine, glycine, lysine isoleucine, valine, tryptophan, arginine, proline, taurine, threonine, histidine, alanine, cysteine, methionine, and/or leucine, where the amount of free amino acids and ratio of phenylalanine to tyrosine is selected to provide pain relief within 5 minutes of consumption by a human subject in need of pain relief. Such a composition can include phenylalanine and tyrosine at a weight ratio of about 3.4 to 1. Such a free amino acid preparation can provide cysteine, methionine, and/or leucine in an encapsulated form and the remaining free amino acids as a powder, solution, or suspension. The free amino acid composition can be formulated to provide about 22.7 mg of phenylalanine and or about 133 mg of glycine per kg of lean body weight to a person in need of treatment.

Another embodiment of the inventive concept is a method of treating pain, where a free amino acid composition as described above is provided, and administered as a unit dose to a person in need of pain relief, where the unit dose includes about 22.7 mg of phenylalanine per kg of lean body weight of the person. The free amino acid composition can be provided as a two part formulation, such as a formulation having a powder portion and an encapsulated portion where the encapsulated portion includes the cysteine, methionine, and/or leucine content of the free amino acid composition. In some embodiments the powder portion is dissolved or suspended in a potable liquid prior to administration. Alternatively, the free amino acid composition can be provided as a two part formulation that has a liquid portion and an encapsulated portion, where the encapsulated portion includes the cysteine, methionine, and/or leucine content of the free amino acid composition.

Another embodiment of the inventive concept is a kit for providing a free amino acid preparation effective in treating pain. Such a kit includes a free amino acid composition as described above, where the free amino acid formulation is provided as an encapsulated portion and a powder portion, and where the encapsulated portion includes the cysteine, methionine, and/or leucine content of the free amino acid composition. The kit also includes instructions for use, which in turn include directions to dissolve or suspend the powder portion in a potable liquid prior to consumption. Such instructions can also include directions for adjusting dosage relative to lean body weight, and for factors such as gender, age, and disease state of the person to be treated.

Another embodiment of the inventive concept is a kit for providing a free amino acid preparation effective in treating pain. Such a kit includes a free amino acid composition as described above, where the free amino acid formulation is provided as an encapsulated portion and a liquid portion, and where the encapsulated portion includes the cysteine, methionine, and/or leucine content of the free amino acid composition. The kit also includes instructions for use, which in turn include directions to dissolve or suspend the powder portion in a potable liquid prior to consumption. Such instructions can also include directions for adjusting dosage relative to lean body weight, and for factors such as gender, age, and disease state of the person to be treated.

Another embodiment of the inventive concept is an amino acid preparation for human consumption, which includes a free amino acid preparation consisting of free amino acid forms of glutamine, glycine, lysine isoleucine, valine, phenylalanine, tyrosine, tryptophan, arginine, proline, taurine, threonine, histidine, alanine, cysteine, methionine, and leucine, wherein the weight ratios of glutamine:glycine:lysine:isoleucine:valine:phenylalanine:tyrosine:tryptophan:arginine:proline:taurine:threonine:histidine:alanine:cysteine:methionine:leucine of about 3:10:2.1:1.4:1.8:1.7:0.5:0.3:1:1:0.5:1.1:0.7:2:0.5:1.1:2.7.

Another embodiment of the inventive concept is a kit for providing a free amino acid preparation effective in treating pain. Such a kit includes a free amino acid preparation consisting of free amino acid forms of glutamine, glycine, lysine, isoleucine, valine, phenylalanine, tyrosine, tryptophan, arginine, proline, taurine, threonine, histidine, alanine, cysteine, methionine, and leucine, wherein the weight ratios of glutamine:glycine:lysine:isoleucine:valine:phenylalanine:tyrosine:tryptophan:arginine:proline:taurine:threonine:histidine:alanine:cysteine:methionine:leucine of about 3:10:2.1:1.4:1.8:1.7:0.5:0.3:1:1:0.5:1.1:0.7:2:0.5:1.1:2.7. The free amino acid formulation is provided as an encapsulated portion and a powder portion, where the encapsulated portion comprises cysteine, methionine, and leucine content of the free amino acid composition. The kit also includes instructions for use, which in turn include directions to dissolve or suspend the powder portion in a potable liquid prior to consumption. The instructions for use can also include direction for adjusting dosage relative to lean body weight, and for factors such as gender, age, and disease state of the person to be treated.

Another embodiment of the inventive concept is a kit for providing a free amino acid preparation effective in treating pain. Such a kit includes a free amino acid preparation consisting of free amino acid forms of glutamine, glycine, lysine isoleucine, valine, phenylalanine, tyrosine, tryptophan, arginine, proline, taurine, threonine, histidine, alanine, cysteine, methionine, and leucine, wherein the weight ratios of glutamine:glycine:lysine:isoleucine:valine:phenylalanine:tyrosine:tryptophan:arginine:proline:taurine:threonine:histidine:alanine:cysteine:methionine:leucine of about 3:10:2.1:1.4:1.8:1.7:0.5:0.3:1:1:0.5:1.1:0.7:2:0.5:1.1:2.7. The free amino acid formulation is provided as an encapsulated portion and a liquid portion, where the encapsulated portion comprises cysteine, methionine, and leucine content of the free amino acid composition. The kit also includes instructions for use, which can include directions for adjusting dosage relative to lean body weight, and for factors such as gender, age, and disease state of the person to be treated.

Various objects, features, aspects and advantages of the inventive subject matter will become more apparent from the following detailed description of preferred embodiments, along with the accompanying drawing FIGURES in which like numerals represent like components.

DETAILED DESCRIPTION

The inventive subject matter provides a composition in which the active ingredient is composed of free amino acids, where the composition is useful for providing rapid (i.e. less than five minutes in onset) relief of pain following consumption, and methods for using the composition. For the purposes of this application the term "free amino acid" is inclusive of both free base and salt (i.e. complexed with counterion) forms of individual amino acids. Surprisingly, the Inventor has found that providing a composition in which the active portion includes essential and conditionally essential amino acids in free form and in certain weight ratios relative to each other provides rapid and effective relief of pain from a variety of sources, including migraine. In particular, the Inventors have found that a free amino acid supplement in which the leucine:isoleucine:valine weight ratio is about is about 1.9:1:1.3 has a significant and lasting effect in this regard. Within the context of this application the term "about" indicates a range of ±20% of the stated value.

One should appreciate that the disclosed techniques provide many advantageous technical effects including rapid and effective relief of pain in a human subject using a relatively simple formulation of free amino acids, which are highly defined and readily available. Such a formulation can advantageously be highly effective while excluding non-steroidal anti-inflammatory drugs, steroids, opioids, and herbal extracts (which are poorly characterized and difficult to reproduce).

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

An example of a suitable free amino acid composition is shown below. It should be appreciated that not all of the free amino acids listed be present to provide a useful effect, provided that the relative weight ratios between the included amino acids is maintained. For example, in a composition that does not include all of the free amino acids listed in Table 1, a weight ratio of leucine:isoleucine:valine of about 1.9:1:1.3 can be maintained. The amounts shown can be varied by ±20% while retaining effectiveness.

TABLE 1

| Free Amino Acid | mg/kg lean body weight |
| --- | --- |
| Glutamine | 40.0 |
| Glycine | 133.3 |
| Lysine | 28.0 |
| Isoleucine | 18.7 |
| Valine | 24.0 |
| Phenylalanine | 22.7 |
| Tyrosine | 6.7 |
| Tryptophan | 4.0 |
| Arginine | 13.3 |
| Proline | 13.3 |
| Taurine | 6.7 |
| Threonine | 14.7 |
| Histidine | 9.3 |
| Alanine | 26.7 |
| Cysteine | 6.7 |
| Methionine | 14.7 |
| Leucine | 36.0 |

In some embodiments the free amino acid preparation is provided as a two part formulation. Surprisingly, the Inventor has found that the inclusion of certain free amino acids (for example, alanine) improves the palatability of the free amino acid preparation without the need to include sugars or other flavorants. As such sugars, sugar alcohols, artificial sweeteners, and other flavorants can be excluded from a free amino acid preparation of the inventive concept while retaining effectiveness and palatability. Such a two part formulation can include a combination of free amino acids mixed together in powder form (or, alternatively, as a solution or liquid suspension) as one part of the two-part formulation. Certain free amino acids useful to the preparation have been found to be unpalatable and/or to contribute to a lack of palatability when mixed with others, and can be provided in an encapsulated or tablet form as a second part of the two part formulation. Examples of amino acids that contribute to unpleasant taste are cysteine, methionine, and/or leucine.

Free amino acids can be derived from any suitable source, including animal proteins, plant proteins, bacterial proteins, fungal proteins, and organic synthesis. In a preferred embodiment free amino acids are obtained in a renewable fashion from plant proteins, for example by enzymatic digestion and/or acid hydrolysis of proteins obtained from renewable plant sources (e.g. grains). Suitable formulations can be prepared from free amino acids of at least 90%, 95%, 98%, 99%, or greater than 99% purity.

Preparations of the inventive concept can be formulated to provide an effective amount of the free amino acids contained therein. This amount can be adjusted according to body weight, and in preferred embodiments can be adjusted according to lean body weight (i.e. body weight adjusted for nominal fat composition). For example, an individual with a lean body weight of 75 kg can consume an amount of a preparation of the inventive concept that provides leucine:isoleucine:valine in a weight ratio of about 1.9:1:1.3 (e.g. about 2.7 g leucine, about 1.4 g isoleucine, and about 1.8 g valine) to achieve a desired pain-relief effect, whereas a smaller individual with a lean body weight of 50 kg can consume an amount of a preparation of the inventive concept that provides about 1.8 g leucine, about 0.9 g isoleucine, and about 1.2 g valine to obtain a similar effect. Dosages can be adjusted upwards in a similar, linear fashion for larger individuals. For a preparation prepared as in Table 1, it was found that a suitable dosage could be provided by calculating 0.19 g of total free amino acids per pound of lean body weight.

Dosage can also be adjusted for other factors, such as age, gender, and/or disease state. For example dosage can be adjusted for lean body weight and modified by the adding an additional 10% when used by children. Similarly, dosage can be adjusted by an additional 5%, 10%, 15%, 20% or more for persons with diabetes, irritable bowel syndrome, autoimmune disease, cancer, and other conditions. Alternatively, dosage can be adjusted downwards by 5%, 10%, 15%, 20%, 25% or more in individuals with impaired kidney and/or liver functions. In a preferred embodiment the ratios between the respective free amino acids as described above are maintained when such adjustments are made. In some embodiments certain amino acids can be reduced or eliminated from the formulation to accommodate individuals with specific metabolic and/or genetic issues that affect amino acid processing. For example, phenylalanine can be reduced or eliminated in formulations provided to persons with phenylketonuria.

In some embodiments a preparation of the inventive concept can be provided as a kit, along with directions for use. Such a kit can include a volumetric measuring device (such as a scoop, measuring spoon, syringe, and/or graduated vessel) suitable for portioning a dry powder or liquid portion of the preparation. Similarly, the encapsulated portion of such a formulation can be provided as multiple encapsulated unit doses, where each unit dose corresponds to a convenient weight increment. For example, a single encapsulated unit dose can include an amount of free amino acid mixture suitable for use for 5 kg, 10 kg, 15 kg, 20 kg, 25 kg, or more than 25 kg of body weight, permitting dosage control by consumption of a suitable number of unit dose capsules. Directions for use can include a dosing schedule, for example in the form of a table, that describes recommended doses, frequency of dosing (e.g. as needed, or from three times a day to once a week), and directions for dissolving or suspending a dry powder formulation in a suitable potable liquid (for example water, tea, coffee, or fruit juice). Suitable dosing schedules provide a frequency of administration of every 4 hours, every 6 hours, every 8 hours, twice a day, once a day, every two days, every 3 days, once a week, once every two weeks, once a month, or longer intervals. In a preferred embodiment, dosing occurs once a day as needed for pain. Dosing schedules can include a period of treatment ranging from one time use, for a period of 1 week, for a period of 2 weeks, for a period of 1 month, for a period of 2 months, for a period of 3 months, for a period of 6 months, or for a period of a year or more. In some embodiments the period of treatment extends through the remainder of the individual's life. The dosage amount and schedule can be modified during the treatment period to reflect changes in the individual's condition and/or body composition.

The Inventor has observed that preparations of the inventive concept are effective in providing rapid (i.e. less than five minutes) and persistent reduction or elimination of pain, for example pain originating from migraine headaches and/or from kidney stones. This pain relief is frequently immediate and can be achieved without the use of additional medications such as nonsteroidal anti-inflammatory drugs (NSAIDs) or opiates. Without wishing to be bound by theory, the Inventor believes that this is related to substantial release and/or increased synthesis of dopamine. The Inventor has also observed that formulations of the inventive concept are effective in reducing joint pain, reducing and/or eliminating seizures, reducing insulin requirements in diabetes (for example, by about 90%), reducing or eliminating the symptoms of attention deficit disorder, reducing or eliminating the symptoms of chronic fatigue syndrome, and promoting skin tone, nail growth, and general health. The Inventor has also observed increased muscle strength and improved recovery from the side effects of chemotherapy and radiation therapy (particularly lack of energy). Significant (e.g. about 50%) reduction in observed tumor volume was also observed during a two week treatment period with a preparation of the inventive concept, indicating that such preparations can have anti-neoplastic activity. These results were obtained without reported or observed adverse side effects.

It should be appreciated that while additional compounds such as nonsteroidal anti-inflammatory drugs, opiates, steroids, and herbal extracts with similar activities do not need to part of a formulation of the inventive concept in order for it to be effective, such compounds can be used in conjunction and/or in a complementary fashion with a free amino acid preparation of the inventive concept in some embodiments. Preparations of the inventive concept can also be used in conjunctions with compounds such as Botox™ (which is used for relief of migraine) and/or Adderall™ or other pharmaceutical compounds used to treat the symptoms of attention deficit disorder. In some embodiments a preparations of the inventive concept can include or be used in conjunction with compounds that can potentiate their activity, for example caffeine and/or theobromine. Such potentiating compounds can be included as part of the free amino acid formulation or can be provided by ancillary means (for example, by consumption with coffee, tea, and/or caffeine-containing soft drinks).

Similarly, it is not necessary to include other additional compounds (e.g. vitamins, minerals, organic acids, etc.) that have been associated with the use of free amino acid supplements for the compositions described above to be effective. For example, inclusion of one or more vitamin(s) and/or enzyme cofactor(s) associated with the use of free amino acids (e.g. vitamin A, a B vitamin, vitamin B1, vitamin B6, vitamin B12, vitamin C, a D vitamin, vitamin E, vitamin K, riboflavin, folate, thiamin, pantothenic acid, biotin, coenzyme Q, etc.) is not necessary for the formulation of a nutritional supplement of the inventive concept. Similarly, inclusion of organic acids (e.g. acetic acid, ascorbic acid, citric acid, lactic acid, malic acid, fumaric acid, etc.) and/or salts thereof associated with free amino acid compositions in formulations of the inventive concept is not necessary. Minerals and trace elements associated with free amino acid compositions (such as calcium, magnesium, iodine, iron, zinc, selenium, copper, manganese, molybdenum, chromium, etc.) are similarly not necessary ingredients of formulations of the inventive concept. It should be appreciated that while additional components such as vitamins, enzyme cofactors, organic acids, and/or minerals do not need to part of a formulation of the inventive concept in order for it to be effective, such components can be used in conjunction and/or in a complementary fashion with a free amino acid preparation of the inventive concept in some embodiments.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. An amino acid preparation for human consumption, comprising:
    free amino acid forms of phenylalanine in powder, solution, or suspension form, tyrosine in powder, solution, or suspension form, glycine in powder, solution, or suspension form, leucine in encapsulated form, valine in powder, solution, or suspension form, isoleucine in powder, solution, or suspension form, alanine in powder, solution or suspension form, and at least one of cysteine in encapsulated form, methionine in encapsulated form, glutamine in powder, solution, or suspension form, lysine in powder, solution, or suspension form, tryptophan in powder, solution, or suspension form, arginine in powder, solution, or suspension form, proline in powder, solution, or suspension form, taurine in powder, solution, or suspension form, threonine in powder, solution, or suspension form, histidine in powder, solution, or suspension form, wherein the weight ratio of leucine:isoleucine:valine is about 1.9:1:1.3.

2. The preparation of claim 1, wherein the preparation comprises phenylalanine and is formulated to provide about 22.7 mg of phenylalanine per kg of lean body weight per day to a user in need of treatment of pain.

3. The preparation of claim 1, wherein the preparation is formulated to provide about 133 mg of glycine per kg of lean body weight per day to a user in need of treatment of pain.

4. A kit for providing a free amino acid preparation effective in treating pain, comprising:
    a free amino acid composition comprising free amino acid forms of phenylalanine in powder form, tyrosine in powder form, glycine in powder form, alanine in powder form, and at least one free amino acid selected from the group consisting of glutamine in powder form, lysine in powder form, isoleucine in powder form, valine in powder form, tryptophan in powder form, arginine in powder form, proline in powder form, taurine in powder form, threonine in powder form, histidine in powder form, alanine in powder form, cysteine in encapsulated form, methionine in encapsulated form, and leucine in encapsulated form, wherein the weight ratio of phenylalanine:tyrosine:glycine is 3.4:1:19.9; and
    instructions for use, wherein the instructions for use comprise directions to dissolve or suspend powder content of the kit in a potable liquid prior to consumption.

5. The kit of claim 4, comprising cysteine in encapsulated form, methionine in encapsulated form, and leucine in encapsulated form, and wherein the instructions for use comprise direction for adjusting dosage relative to a factor selected from the group consisting of lean body weight, age, gender, and disease state.

6. A kit for providing a free amino acid preparation effective in treating pain, comprising:
   a free amino acid composition comprising free amino acid forms of phenylalanine in liquid form, tyrosine in liquid form, glycine in liquid form, alanine in liquid form, and at least one free amino acid selected from the group consisting of glutamine in liquid form, lysine in liquid form, isoleucine in liquid form, valine in liquid form, tryptophan in liquid form, arginine in liquid form, proline in liquid form, taurine in liquid form, threonine in liquid form, histidine in liquid form, alanine in liquid form, cysteine in encapsulated form, methionine in encapsulated form, and leucine in encapsulated form, wherein the weight ratio of phenylalanine:tyrosine:glycine is 3.4:1:19.9; and
   instructions for use.

7. The kit of claim 6, comprising cysteine in encapsulated form, methionine in encapsulated form, and leucine in encapsulated form, and wherein the instructions for use comprise direction for adjusting dosage relative to a factor selected from the group consisting of lean body weight, age, gender, and disease state.

8. An amino acid preparation for human consumption, comprising:
   a free amino acid preparation consisting of free amino acid forms of glutamine, glycine, lysine isoleucine, valine, phenylalanine, tyrosine, tryptophan, arginine, proline, taurine, threonine, histidine, alanine, cysteine, methionine, and leucine, wherein the weight ratio of glutamine:glycine:lysine:isoleucine:valine:phenylalanine:tyrosine:tryptophan:arginine:proline:taurine:threonine:histidine:alanine:cysteine:methionine:leucine is 10:33.3:7:4.7:6:5.7:1.7:1:3.3:3.3:1.7:3.7:2.3:6.7:1.7:3.7:9.

9. A kit for providing a free amino acid preparation effective in treating pain, comprising:
   a free amino acid composition consisting of free amino acid forms of glutamine in powder form, glycine in powder form, lysine in powder form, isoleucine in powder form, valine in powder form, phenylalanine in powder form, tyrosine in powder form, tryptophan in powder form, arginine in powder form, proline in powder form, taurine in powder form, threonine in powder form, histidine in powder form, alanine in powder form, cysteine in encapsulated form, methionine in encapsulated form, and leucine in encapsulated form, wherein the weight ratio of glutamine:glycine:lysine:isoleucine:valine:phenylalanine:tyrosine:tryptophan:arginine:proline:taurine:threonine:histidine:alanine:cysteine:methionine:leucine content is 10:33.3:7:4.7:6:5.7:1.7:1:3.3:3.3:1.7:3.7:2.3:6.7:1.7:3.7:9; and
   instructions for use, wherein the instructions for use comprise directions to dissolve or suspend amino acids provided in powder form in a potable liquid prior to consumption.

10. The kit of claim 9, wherein the instructions for use comprise direction for adjusting dosage relative to a factor selected from the group consisting of lean body weight, age, gender, and disease state.

11. A kit for providing a free amino acid preparation effective in treating pain, comprising:
   a free amino acid composition consisting of a liquid formulation consisting of free amino acid forms of glutamine, glycine, lysine isoleucine, valine, phenylalanine, tyrosine, tryptophan, arginine, proline, taurine, threonine, histidine, and alanine, and an encapsulated formulation consisting of cysteine, methionine, and leucine, wherein the weight ratio of glutamine:glycine:lysine:isoleucine:valine:phenylalanine:tyrosine:tryptophan:arginine:proline:taurine:threonine:histidine:alanine:cysteine:methionine:leucine is 10:33.3:7:4.7:6:5.7:1.7:1:3.3:3.3:1.7:3.7:2.3:6.7:1.7:3.7:9; and
   instructions for use.

12. The kit of claim 11, wherein the instructions for use comprise direction for adjusting dosage relative to a factor selected from the group consisting of lean body weight, age, gender, and disease state.

\* \* \* \* \*